United States Patent
Hill et al.

(10) Patent No.: US 6,713,076 B1
(45) Date of Patent: Mar. 30, 2004

(54) METHODS FOR REMOVING A CONTAMINANT BY A POLYOXOMETALATE-MODIFIED FABRIC OR A POLYOXOMETALATE-MODIFIED CELLULOSIC FIBER AND FABRICS THEREOF

(75) Inventors: Craig L. Hill, Atlanta, GA (US); Ling Xu, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/673,187

(22) PCT Filed: Apr. 12, 1999

(86) PCT No.: PCT/US99/07889

§ 371 (c)(1),
(2), (4) Date: Dec. 4, 2000

(87) PCT Pub. No.: WO99/53131

PCT Pub. Date: Oct. 21, 1999

Related U.S. Application Data

(60) Provisional application No. 60/081,595, filed on Apr. 13, 1998.

(51) Int. Cl.[7] .............................. A61K 9/00; A61K 9/70; A61K 33/24; A01N 25/00; A01N 25/08; A01N 25/32; A01N 59/16; A62D 5/00; A62D 3/00; D06M 11/00; D06M 11/47; D06M 11/48; A61L 9/00

(52) U.S. Cl. .................... 424/402; 424/76.21; 424/405; 424/411; 424/414; 424/443; 424/484; 424/600; 424/601; 424/604; 424/617; 424/646; 424/682; 424/691; 514/974; 588/200

(58) Field of Search ................. 424/402, 484, 424/443, 76.21, 405, 411, 414, 600, 601, 604, 617, 646, 682, 691; 514/974; 588/200

(56) References Cited

U.S. PATENT DOCUMENTS

| | | | |
|---|---|---|---|
| 3,387,916 A | 6/1968 | Clarke .......................... 8/539 |
| 3,504,997 A | 4/1970 | Clapham ....................... 8/529 |
| 3,925,006 A | 12/1975 | Forschirm et al. ............. 8/497 |
| 3,947,332 A | 3/1976 | Vanderpool et al. ........ 205/477 |
| 4,186,243 A | 1/1980 | Astbury et al. ............. 503/201 |
| 4,444,592 A | 4/1984 | Ludwig ..................... 106/413 |
| 4,639,432 A | 1/1987 | Holt et al. .................. 502/324 |
| 4,714,482 A | 12/1987 | Polak et al. ..................... 96/4 |
| 5,071,877 A | 12/1991 | Bannard et al. ............. 514/640 |
| 5,603,927 A | 2/1997 | Fukumoto et al. .......... 424/76.1 |
| 5,607,979 A | 3/1997 | McCreery ................... 514/759 |
| 5,851,948 A | 12/1998 | Chuang et al. ............. 502/314 |
| 2003/0049330 A1 * | 3/2003 | Hill et al. ................... 424/604 |
| 2003/0072811 A1 * | 4/2003 | Hill et al. ................... 424/618 |

FOREIGN PATENT DOCUMENTS

| | | |
|---|---|---|
| DE | 3001657 A1 | 11/1981 |
| GB | 1037990 | 9/1966 |
| JP | 6815758 | 3/1968 |
| JP | 50136488 | 10/1975 |
| JP | 61185568 | 8/1986 |
| JP | 62013464 | 1/1987 |
| JP | 4035716 | 2/1992 |
| JP | 51791788 | 7/1993 |
| JP | 7251075 | 10/1995 |
| SU | 801674 | 7/1979 |
| WO | WO 94/20565 | 9/1994 |
| WO | WO99/53131 | 10/1999 |

OTHER PUBLICATIONS

Hill et al., "Carbon Powder and Fiber–Supported Polyoxometalate Catalytic Materials. Preparation, Characterization, and Catalytic Oxidation of Dialkyl Sulfides as Mustard (HD) Analogues", Chem. Mater. 8, pp. 2523–2527 (1996).

Gall et al., Carbon Powder and Fiber–Supported Polyoxometalate Catalytic Materials, Preparation, Characterization, and Catalytic Oxidation of Dialkyl Sulfides as Mustard (HD) Analogues, *Chem Mater.* 8, 2523–2527 (1996).

Gall et al., "Selective Oxidation of Thioether Mustard (HD) Analogs by tert–Butylhydroperoxide Catalyzed by $H_5PV_2Mo_{10}O_{40}$ Supported on Porous Carbon Materials," *Journal of Catalysis* 159, 473–478 (1996).

Riedel, "Light–Fastness of Pigments in Standard Color Depths," *Farbe Lack*, 74(4) Date Not Available.

Katsoulis, "A Survey of Applications of Polyoxometaletes," *Chemical Reviews*, 98(1), 359–387, 1998.

Hill et al., "The First Cominationally Prepared and Evaluated Inorganic Catalysts. Polyoxomdeletes For the Aerobic Oxidation of Mustard Analog Tetrahydrothiophene (THT)" *Journal of Molecular Catalysis A: Chemical* 114, pp. 103–111, 1996.

Zeng et al., "Catalytically Decontaminating Dendrimers. Poly–tris Arborols Covalently Functionalized With Redox Active Polyoxometalates" Proc. ERDEC Sci. Conf. Chem. Biol. Def. Res., (1998), Meeting Date Nov. 19, 1997; pp. 351–357.

Holleman et al., "Lehrbuch der Anorganischen Chemie", Walter de Gruyter, pp. 1097–1099, 1105–1106 (1985). (German).

* cited by examiner

*Primary Examiner*—John Pak

(57) ABSTRACT

The invention relates to a method for removing a contaminant from a gas phase or a liquid phase by contacting an article composed of (1) a fabric or cellulosic fiber and (2) a polyoxometalate, wherein the polyoxometalate is incorporated in the fabric or cellulosic fiber, with the gas phase or liquid phase containing the contaminant. The invention further relates to a polyoxometalate-modified fabric composed of a fabric and a polyoxometalate of the present invention incorporated in the fabric. The invention further relates to an article containing the polyoxometalate-modified fabric. The invention further relates to a method for making the polyoxometalate-modified fabric, by contacting the fabric with a polyoxometalate to produce a polyoxometalate-modified fabric.

6 Claims, 3 Drawing Sheets

METHODS FOR REMOVING A CONTAMINANT BY A POLYOXOMETALATE-MODIFIED FABRIC OR A POLYOXOMETALATE-MODIFIED CELLULOSIC FIBER AND FABRICS THEREOF

This application is a 371 of PCT/US99/07889, filed on Apr. 12, 1999, and claims benefit of Provisional application No. 60/081,595, filed on Apr. 13, 1998.

FIELD OF THE INVENTION

The present invention relates to methods for removing a contaminant by a polyoxometalate-modified fabric or a polyoxometalate-modified cellulosic fiber from the gas or liquid phase. The invention further relates to polyoxometalate-modified fabrics and articles comprising a polyoxometalate-modified fabric.

BACKGROUND OF THE INVENTION

Decreasing the potential danger of toxic gases has long been a significant issue. Offensive odors originating from cigarette smoke, sweat, exhaust gases, and rotten food in the work place, the home, and elsewhere are caused by thousands of gaseous components. Examples of deleterious and/or foul-smelling compounds include, but are not limited to, acetaldehyde, hydrogen sulfide, methyl mercaptan, ammonia, trimethylamine, and nicotine.

The goal is to fabricate and use self-deodorizing fabrics and cellulosic fibers in the form of clothing, furniture upholstery, curtains, carpets, or paper to remove or degrade gaseous or liquid toxic and/or malodorous compounds in the work place and home. Textiles produced in Japan are known to remove contaminants from the gas phase. Some of the Japanese textiles have carbonate anions or amines incorporated within the fiber. CLEAN GUARD, which is manufactured by Komatsu Seiren Co., LTD of Japan, contains finely divided ceramics and amphoteric oxides as the deodorizing components incorporated within the fabric. Smoklin®, which is a cloth composed of polyacrylic yarn manufactured by Asahi Chemical Industry Company, can also remove contaminants from the gas phase. U.S. Pat. No. 5,603,927 to Fukumoto et al. discloses the incorporation of acid salts of aniline halides, amino benzoic acid, sulfanilamide or derivatives thereof, or aminoacetophenone into a porous carrier such as a fiber or cloth in order to remove offensive odors.

The prior art in this area, however, demonstrates a serious shortcoming, namely that the materials are effective only through stoichiometric physisorption or chemisorption processes based on acid-base, ion pairing (salt formation) and/or oxidation-reduction reactions. Because this technology is stoichiometric and not catalytic, it is not very practical and economical.

The incorporation of a polyoxometalate (herein referred to as "POM") into a fabric or cellulosic fiber in order to remove a contaminant from the gas phase has not been disclosed in the art. Furthermore, the prior art is very limited with respect to the use of a polyoxometalate-modified fabric or cellulosic fiber for the removal of a contaminant from the liquid phase. Gall et al. (Chem. Mat. 8, pp. 2523–2527, 1996) disclose the immobilization of $H_5PV_2Mo_{10}O_{40}$ on carbon cloth in order to determine the ability of $H_5PV_2Mo_{10}O_{40}$ to remove sulfur containing compounds from toluene. However, Gall et al. did not investigate the removal of sulfur containing compounds from the gas phase.

Typically, heteropoly and isopoly acids, which are subsets of polyoxometalates, are used as pigments and dyes when they are incorporated into a fabric. Japanese Patent Application No. JP 50136488 to Kakinuma et al. discloses contacting yarn with a heteropoly acid or tartaric acid to improve the lightfastness of the yarn. Japanese Patent No. JP 82014477 B discloses the lightfastness of yarn is improved when the yarn is contacted with an aqueous solution of phosphomolybdic acid.

JP 5179188, JP 61185568, and JP 62013464 disclose that heteropoly acids such as phosphotungstic acid, phosphomolybdic acid, silicomolybdic acid, silicotungstic acid, phosphotungstomolybdic acid, phosphovanadomolybdic acid, and their salts can be used as colorants and pigments for ink compositions. U.S. Pat. No. 3,947,332 to Vanderpool et al. disclose the synthesis of heteropoly acids containing tungsten or molybdenum and at least one other element having a positive valence from 2 to 7. The heteropoly acids disclosed in Vanderpool et al. can be used in printing inks and paper coloring.

U.S. Pat. No. 3,925,006 to Forschirm et al. discloses first contacting a cellulose ester with sodium tungstophosphate or sodium tungstosilicate followed by contacting the cellulose ester with a cationic dye. The sodium tungstophosphate and sodium tungstosilicate improve the uptake of the cationic dye into the cellulose ester. U.S. Pat. No. 4,444,592 to Ludwig discloses the preparation of a pigment that is the reaction product between a heteropoly acid and pararosaniline. The water insoluble pigment can be used in the textile arts. Chem. Rev. 1998, 98, pp. 359–387 to Katsoulis is a comprehensive review article that discloses the use of POMs as dyes and pigments.

Japanese Patent No. JP 71036516 B discloses a method for resin-treating textile goods containing cellulosic or hydrophobic fibers. The cellulosic fiber is treated with an isopoly or heteropoly acid. The resultant cellulosic fiber possesses increased soil-and-crease resistance and wash-and-wear properties. International Patent Application No. 94/20565 to Jackson et al. discloses contacting an aramid with an aqueous solution of a tungsten compound, preferably phosphotungstic acid and ammonium metatungstate, in order to decrease the flammability of textile articles. None of the references described above disclose the removal of a contaminant from the gas or liquid phase.

A POM-based fixed-bed catalytic reactor for the purification of gas in vents or passages has been disclosed in Japanese Patent Application No. 0435716 to Akio et al. This reactor involves a POM ($H_3PMo_6W_6O_{40}$) immobilized on a porous moulding of cordierite.

Japanese Patent Application No. 7251075 discloses the gas phase oxidation of unsaturated aldehydes to the corresponding carboxylic acid by a heteropoly acid catalyst containing molybdenum and vanadium. The catalyst is used in combination with carbon fibers. There is no disclosure in JP 7251075, however, for the removal of a contaminant from the gas or liquid phase.

In light of the above, it would be very desirable to have an article and a method of using an article for the removal of toxic and/or malodorous compounds without adding stoichiometric amounts of additives or compounds to the article. The present invention solves such a need in the art while providing surprising advantages. The present invention herein incorporates a catalytically active early-transition-metal oxygen anion cluster (polyoxometalate or POM) into textiles, fabrics, and cellulosic fibers, including the Japanese deodorizing fabrics described above, which greatly increases the ability of the fabric to remove toxic, offensive and/or odorous compounds from the gas and liquid phase.

SUMMARY OF THE INVENTION

In accordance with the purpose(s) of this invention, as embodied and broadly described herein, this invention, in one aspect, relates to a method for removing a contaminant from the gas phase, comprising contacting an article comprising a fabric and at least one polyoxometalate, wherein the polyoxometalate is incorporated in the fabric to produce a polyoxometalate-modified fabric, with the gas phase containing the contaminant.

The invention further relates to a method for removing a contaminant from the liquid phase, comprising contacting an article comprising a fabric and at least one polyoxometalate, wherein the polyoxometalate is incorporated in the fabric to produce a polyoxometalate-modified fabric, with the liquid phase containing the contaminant, with the proviso that when the fabric is carbon cloth, then the polyoxometalate is not $H_5PV_2Mo_{10}O_{40}$.

The invention further relates to a method for removing a contaminant from the gas phase or liquid phase, comprising contacting an article comprising a cellulosic fiber and at least one polyoxometalate, wherein the polyoxometalate is incorporated in the cellulosic fiber to produce a polyoxometalate-modified cellulosic fiber, with the gas phase or liquid phase containing the contaminant.

The invention further relates to a polyoxometalate-modified fabric, comprising a fabric and at least one polyoxometalate, wherein the polyoxometalate has the formula $[V_kMo_mW_nNb_oTa_pM_qX_rO_s]^{y-}$[A], wherein M is at least one f-block element or d-block element having at least one d-electron, wherein M is not vanadium, molybdenum, tungsten, niobium, or tantalum; X is at least one p-, d-, or f-block element, wherein X is not oxygen; k is from 0 to 30; m is from 0 to 160; n is from 0 to 160; o is from 0 to 10; p is from 0 to 10; q is from 0 to 30; r is from 0 to 30; s is sufficiently large that y is greater than zero; and y is greater than zero, wherein the sum of k, m, n, o, and p is greater than or equal to four; and the sum of k, m, and q is greater than zero, and A is a counterion, wherein the polyoxometalate is incorporated in the fabric, with the proviso that when A is a proton, the polyoxometalate is not the reaction product between $[V_kMo_mW_nNb_oTa_pM_qX_rO_s]^{y-}$[A] and a pararosaniline compound, with the further proviso that the polyoxometalate is not silicomolybdenic acid or its sodium salt, phosphomolybdenic acid, ammonium chromododecanemolybdenate, ammonium salt of hydrogen bexamolybdocobaltic acid, para-tungstic acid or its ammonium salt or sodium salt, meta-tungstic acid or its ammonium salt or sodium salt, phosphotungstic acid or its salt, silicotungstic acid or its salt, dodecane tungstodicobaltic acid or its salt, phosphotungstomolybdenic acid or its salt, or phosphovanadomolybdenic acid or its salt, with the further proviso that when the fabric is carbon cloth, the polyoxometalate is not $H_5PV_2Mo_{10}O_{40}$.

The invention further relates to an article comprising a polyoxometalate-modified fabric.

The invention further relates to a method of making a polyoxometalate-modified fabric comprising contacting the fabric with the polyoxometalate to produce the polyoxometalate-modified fabric.

Additional advantages of the invention will be set forth in part in the description which follows, and in part will be obvious from the description, or may be learned by practice of the invention. The advantages of the invention will be realized and attained by means of the elements and combinations. It is to be understood that both the foregoing general description and the following detailed description are exemplary and explanatory only and are not restrictive of the invention.

DETAILED DESCRIPTION OF THE INVENTION

Figure 1:
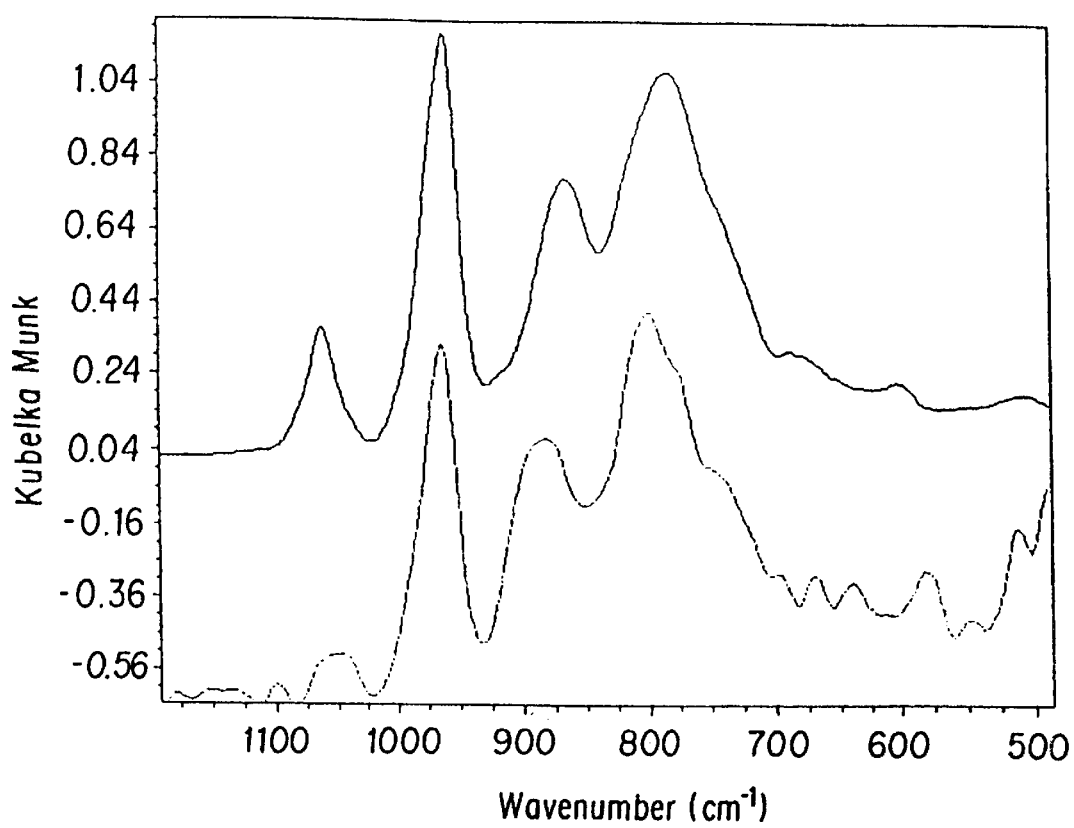
FIG. 1 shows the DRIFT spectra of 1-acrylic (5 wt % of 1, bottom) and unsupported 1 powder (top), where 1 is $H_5PV_2Mo_{10}O_{40}$.

The present invention may be understood more readily by reference to the following detailed description of preferred embodiments of the invention and the Examples included therein.

Before the present methods and articles are disclosed and described, it is to be understood that this invention is not limited to specific synthetic methods or to particular formulations, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings:

The singular forms "a," "an" and "the" include plural referents unless the context clearly dictates otherwise.

"Optional" or "optionally" means that the subsequently described event or circumstance may or may not occur, and that the description includes instances where said event or circumstance occurs and instances where it does not.

In accordance with the purpose(s) of this invention, as embodied and broadly described herein, this invention, in one aspect, relates to a method for removing a contaminant from the gas phase, comprising contacting an article comprising a fabric and at least one polyoxometalate, wherein the polyoxometalate is incorporated in the fabric to produce a polyoxometalate-modified fabric, with the gas phase containing the contaminant.

The invention further relates to a method for removing a contaminant from the liquid phase, comprising contacting an article comprising a fabric and at least one polyoxometalate, wherein the polyoxometalate is incorporated in the fabric to produce a polyoxometalate-modified fabric, with the liquid phase containing the contaminant, with the proviso that when the fabric is carbon cloth, then the polyoxometalate is not $H_5PV_2Mo_{10}O_{40}$.

The invention further relates to a method for removing a contaminant from the gas phase or liquid phase, comprising contacting an article comprising a cellulosic fiber and at least one polyoxometalate, wherein the polyoxometalate is incorporated in the cellulosic fiber to produce a polyoxometalate-modified cellulosic fiber, with the gas phase or liquid phase containing the contaminant.

Many polyoxometalates known in the art can be used in the present invention to remove a contaminant from the gas phase. Polyoxometalates are also referred to in the art as heteropoly compounds, heteropoly acids, isopoly compounds, and isopoly acids, which are subsets of polyoxometalates. Examples of polyoxometalates useful in the present invention are disclosed in Pope, M. T. in *Heteropoly and Isopoly Oxometalates*, Springer Verlag, 1983, and *Chemical Reviews*, vol. 98, no. 1, pp. 1–389, 1998, which are incorporated by this reference in their entirety.

The selection of the polyoxometalate used in the present invention is dependent upon the contaminant or contaminants to be removed from the gas phase or liquid phase. In one embodiment, the polyoxometalate has the formula $[V_kMo_mW_nNb_oTa_pM_qX_rO_s]^{y-}[A]$ wherein M is at least one f-block element or d-block element having at least one d-electron, wherein M is not vanadium, molybdenum, tungsten, niobium, or tantalum; X is at least one p-, d-, or f-block element, wherein X is not oxygen; k is from 0 to 30; m is from 0 to 160; n is from 0 to 160; o is from 0 to 10; p is from 0 to 10; q is from 0 to 30; r is from 0 to 30; s is sufficiently large that y is greater than zero; and y is greater than zero, wherein the sum of k, m, n, o, and p is greater than or equal to four; and the sum of k, m, and q is greater than zero, and A is a counterion. In one embodiment, s is from 19 to 460. The charge on the POM, y, is dictated by the values of k, m, n, o, p, q, r and s. The p-, d-, and f-bock elements can exist in any oxidation state.

The counterion A can be any counterion known in the art. Examples of counterions include, but are not limited to, quaternary ammonium cation, proton, alkali metal cation, alkaline earth metal cation, ammonium cation, d-block cations, f-block cations, or a combination thereof. In one embodiment, the polyoxometalate is an acid, wherein the counterion A is $H^+$. In one embodiment, the counterion is a d- or f-block metal complex. In one embodiment, the counterion is trimethyl-triazacyclononane manganese. In another embodiment, the counterion is silver or gold. Not wishing to be bound by theory, it is believed that some counterions of the present invention can be reduced to the corresponding metal when the polyoxometalate contacts the contaminant. For example, when the cation is $Ag^{+1}$ or $Au^{+1}$, these cations can be reduced to silver metal or gold metal, respectively, depending upon the contaminant that is to be removed.

Generally, M can be any d-block element having at least one d-electron. Typically, M comprises titanium, chromium, manganese, cobalt, iron, nickel, copper, rhodium, silver, palladium, platinum, mercury, or ruthenium. In a preferred embodiment, M comprises manganese, cobalt, or ruthenium. In another embodiment, X comprises phosphorus, silicon, aluminum, boron, cobalt, zinc, or iron. When the polyoxometalate has the Keggin structure $XM_{12}$, then it is possible for X and at least one M to be the same d- or f-block element. Not wishing to be bound by theory, it is believed that the metal ion M of the polyoxometalate of the present invention is responsible for removing the contaminant from the gas phase, while X, when present, provides structural integrity to the polyoxometalate.

In one embodiment, the sum of k and q is greater than or equal to one, the sum of k, m, n, o, p, and q is 12, and s is 40. In yet another embodiment, k is not zero. In another embodiment, q is not zero. In a preferred embodiment, the polyoxometalate comprises $H_5PV_2Mo_{10}O_{40}$, $H_4PVMo_{11}O_{40}$, $H_6PV_3Mo_9O_{40}$, $Na_9PV_6Mo_6O_{40}$, $Na_5H_2PV_4Mo_8O_{40}$, or $K_8Co_2W_{11}O_{39}$.

In another embodiment, the polyoxometalate has the formula $[X^{g+}V_bM^{h+}_cZ_{12-b-c}O_{40}]^{u-}[A]$, wherein X is at least one p-, d-, or f-block element; g+ is the charge of X; M is at least one f-block element or d-block element having at least one d-electron, wherein M is not vanadium; h+ is the charge of M; Z is tungsten, molybdenum, niobium, or a combination thereof; b is from 0 to 6; c is from 0 to 6, wherein the sum of b and c is greater than or equal to one; u is greater than 3; and A is a counterion.

In another embodiment, the polyoxometalate has the formula $[X^{g+}V_bZ^{12-b}O_{40}]^{u-}[A]$, wherein X is at least one phosphorus, silicon, aluminum, boron, zinc, cobalt, or iron; Z comprises tungsten, molybdenum, niobium, or a combination thereof; b is from 1 to 6; and u is greater than 3.

In another embodiment, the polyoxometalate has the structure $[X^{g+}M^{h+}_cZ_{12-c}O_{40}]^{u-}[A]$, wherein X is at least one phosphorus, silicon, aluminum, boron, zinc, cobalt, or iron; Z comprises tungsten, molybdenum, niobium, or a combination thereof; $M^{h+}$ is at least one f-block element or d-block element having at least one d-electron; c is from 1 to 6; and u is greater than 3.

In another embodiment, the polyoxometalate has the formula $[X^{i+}_2V_uM^{j+}_vZ_{18-u-v}O_{62}]^{w-}[A]$, wherein X is at least one p-, d-, or f-block element; i+ is the charge of X; M is at least one d- or f-block element, wherein M is not vanadium; j+ is the charge of M; Z is tungsten, molybdenum, niobium, or a combination thereof, u is from 0 to 9; v is from 0 to 9, wherein the sum of u and v is greater than or equal to one; w is greater than or equal to 4; and A is a counterion.

In another embodiment, the polyoxometalate has the formula $[X^{i+}_2V_uZ_{18-v}O_{62}]^{w-}[A]$, wherein X is at least one phosphorus, sulfur, silicon, aluminum, boron, zinc, cobalt, or iron; Z comprises tungsten, molybdenum, niobium, or a combination thereof; u is from 1 to 9; and w is greater than or equal to 4.

In another embodiment, the polyoxometalate has the formula $[X^{i+}_2M_{j+v}Z_{18-v}O_{62}]^{w-}[A]$, wherein X is at least one phosphorus, sulfur, silicon, aluminum, boron, zinc, cobalt, or iron; Z comprises tungsten, molybdenum, niobium, or a combination thereof; $M^{j+}$ is at least one d- or f-block element; v is from 1 to 9; and w is greater than or equal to 4.

In another embodiment, the polyoxometalate has the formula $[YV_xZ_{12-x}O_{40}][A]$, wherein Y is phosphorus, silicon, or aluminum; Z is tungsten or molybdenum; x is from 1 to 6, and A is a counterion. In one embodiment, Y is phosphorus and Z is molybdenum. In one embodiment, Y is phosphorus and Z is tungsten. In one embodiment, Y is silicon and Z is molybdenum. In one embodiment, Y is silicon and Z is tungsten. In one embodiment, Y is aluminum and Z is tungsten. In one embodiment, Y is aluminum and Z is molybdenum.

Polyoxometalates having an organic group, such as an alkyl group or aryl group, an organosilyl group, or other p- or d-block organometallic groups bonded to the POM can also be used in the present invention. The organic group can be branched or straight chain alkyl, alkenyl, or alkynyl group or an aryl group of $C_1$ to $C_{30}$. The alkyl group can also be a polyether or polyol. Not wishing to be bound by theory, the organic group is bonded to the polyoxometalate as depicted in Scheme 1, where R is the organic group:

The reaction between an alcohol and the polyoxometalate I results in the loss of water and the formation of the polyoxometalate II, wherein the organic group is bonded to an oxygen atom of the polyoxometalate. Any alcohol known in the art can be used in the present invention. Examples of alcohols that can be used include, but are not limited to, methanol, ethanol, or tris(hydroxymethyl)methane. The polyoxometalates having organic groups bonded to the POM that are disclosed in Gouzerh et al., *Chem. Rev.*, 98, pp. 77–111, 1998, which is incorporated by reference in its entirety, are useful in the present invention.

In another embodiment, the polyoxometalate I can be reacted with a compound having the generic formula $YA_oR_{4-o}$, wherein Y is silicon, tin, or an other p- or d-block element; A is a leaving group; R is an organic group, such as an alkyl, alkenyl, or alkynyl group or an aryl group of $C_1$ to $C_{30}$; and o is from 1 to 4. Suitable leaving groups for A include, but are not limited to, halides and alkoxides. In Scheme I, the oxygen of polyoxometalate I displaces A from YAR$_3$ to form a new Y-O bond (compound III). Any silyl, tin, or organic derivative of a p- or d-block element known in the art can be used in the present invention, provided that the compound has at least one leaving group. Typically, Met in Scheme I is vanadium, molybdenum, tungsten, niobium, or tantalum.

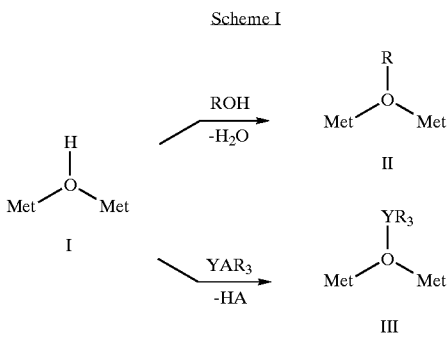

Scheme I

A POM of the present invention can be incorporated into any fabric known in the art to produce a polyoxometalate-modified fabric of the present invention. In one embodiment, fabrics used to prepare garments, draperies, carpets, and upholstery can be used and articles made from them are a part of this invention. In another embodiment, the fabric can be a knit or non-woven fabric. Fibers useful in preparing the polyoxometalate-modified fabrics include, but are not limited to, polyamide, cotton, polyacrylic, polyacrylonitrile, polyester, polyvinylidine, polyolefin, polyurethane, polytetrafluoroethylene, or carbon cloth, or a combination thereof. In one embodiment, the fabric is prepared from cotton, polyacrylic, or polyacrylonitrile. In one embodiment, the fabric is prepared from a cationic fiber. In another embodiment, the fabric comprises (1) a 50/50 blend of nylon-6,6 and cotton or (2) stretchable carbon blended with polyurethane.

Any cellulosic fiber can be incorporated by a POM to produce a polyoxometalate-modified cellulosic fiber of the present invention. Examples of useful cellulosic fibers include, but are not limited to, wood or paper. In a preferred embodiment, a polyoxometalate of the present invention can be incorporated in paper in order to remove a contaminant from the gas or liquid phase. In one embodiment, the paper is wallpaper.

The amount of polyoxometalate incorporated in the fabric and cellulosic fiber also varies depending upon the contaminant to be removed. There is no restriction on the amount of POM that can be incorporated into the fabric or cellulosic fiber. In one embodiment, the amount of polyoxometalate incorporated in the fabric is from 2.5 to 60%, 2.5 to 35%, 2.5 to 30%, 2.5 to 25%, 2.5 to 20%, and 2.5 to 15% based on the total weight of the polyoxometalate-modified fabric or cellulosic fiber.

In one embodiment, the polyoxometalate is $H_5PV_2Mo_{10}O_{40}$ and the fabric is prepared from a polyacrylic fiber. In another embodiment, the polyoxometalate is $H_5PV_2Mo_{10}O_{40}$ and the fabric is prepared from cotton.

In one embodiment, the polyoxometalate is $H_5PV_2Mo_{10}O_{40}$ and the cellulosic fiber is paper.

The present invention is capable of removing a single contaminant or multiple contaminants from the gas or liquid phase. The term "remove" refers to, but is not limited to, the degradation of the contaminant, the conversion of the contaminant into another compound that is either less toxic or nontoxic and/or malodorous, or the adsorption of the contaminant by the polyoxometalate. The POM can degrade the contaminant by a number of different mechanisms. For example, the POM can aerobically oxidize the contaminant acetaldehyde (CH$_3$CHO). Not wishing to be bound by theory, it is believed that the aerobic oxidation of CH$_3$CHO proceeds by a radical chain mechanism (i.e., the initiation of the radical chain by CH$_3$CHO+POM$_{ox \rightarrow CH3}$CO+HPOM$_{red}$).

Contaminants that can be removed by using the present invention include, but are not limited to, aliphatic nitrogen compounds such as amines and ammonia; sulfur-containing compounds such as hydrogen sulfide, thiols, thiophenes, and thioethers; halogenated compounds; and aliphatic oxygenated compounds, such as aldehydes, ketones, organic acids, and alcohols. In one embodiment, the contaminant is acetaldehyde, methyl mercaptan, ammonia, hydrogen sulfide, methyl sulfide, dimethyl sulfide, dimethyl disulfide, trimethylamine, styrene, propionic acid, n-butyric acid, n-valeric acid, iso-valeric acid, or a combination thereof. In another embodiment, the polyoxometalate-modified fabrics and cellulosic fibers can remove mircobial life from the gas or liquid phase. Examples of microbial life include, but are not limited to, bacteria and protozoa.

The present invention can remove a contaminant from the gas phase under mild conditions. In one embodiment, the contaminant can be removed at from −50° C. to 105° C. at a pressure of from 0.1 to 30 atm, preferably from 25° C. to 105° C. at 1 atm. In a preferred embodiment, the present invention can remove a contaminant from the gas phase at room temperature (approximately 25° C.) and at 1 atm. These conditions are very mild when compared to industrial catalysts, which require much higher reaction temperatures and pressures in order to promote catalytic activity. In another embodiment, the present invention can remove a contaminant from the gas phase that has a partial pressure of from 0.1 ppb to 2 atm, 10 ppb to 2 atm, 100 ppb to 2 atm, 200 ppb to 2 atm, and 0.5 ppm to 2 atm. Similarly, the present invention can remove a contaminant from the liquid phase under mild conditions. In one embodiment, the contaminant can be removed from a liquid media at from 0° C. to 200° C. The temperature depends upon the liquid media that is being contacted and the contaminant to be removed.

The gas or liquid phase containing the contaminant can be contacted by the polyoxometalate-modified fabric or cellulosic fiber using a variety of techniques. For example, when the contaminant is in the liquid phase, the polyoxometalate-modified fabric or cellulosic fiber can be dipped or submersed into the liquid phase. Alternatively, the liquid phase can be filtered or passed through the polyoxometalate-modified fabric or cellulosic fiber. When the contaminant is in the gas phase, the polyoxometalate-modified fabric or cellulosic fiber is typically placed in an open or closed environment that contains the contaminant(s).

The POM modified fabrics and cellulosic fibers of the present invention have a number of advantages over the prior art fabrics and fibers that do not use a polyoxometalate to remove a contaminant from the gas or liquid phase. One advantage is that the POM modified fabrics and cellulosic fibers are significantly more effective in deodorization when compared to a fabric or fiber that is not modified with a POM of the present invention. Another advantage is that the present invention can remove a contaminant from the gas or liquid phase starting within milliseconds of contact and can remove the contaminant for extended periods of time, such as several days or longer. The POMs used in the present invention are capable of being regenerated to an active form that permits the removal of the contaminant. Another advantage is that some POMs can render the fabric or cellulosic fiber more water resistant and increase the surface area of the fabric or fiber. Finally, the POM can enhance the dyeability, light fastness, color fastness, and weaving properties of the fabric or cellulosic fiber.

The invention further relates to a polyoxometalate-modified fabric, comprising a fabric and at least one polyoxometalate, wherein the polyoxometalate has the formula $[V_kMo_mW_nNb_oTa_pM_qX_rO_s]^{y-}[A]$, wherein M is at least one f-block element or d-block element having at least one d-electron, wherein M is not vanadium, molybdenum, tungsten, niobium, or tantalum; X is at least one p-, d-, or f-block element, wherein X is not oxygen; k is from 0 to 30; m is from 0 to 160; n is from 0 to 160; o is from 0 to 10; p is from 0 to 10; q is from 0 to 30; r is from 0 to 30; s is sufficiently large that y is greater than zero; and y is greater than zero, wherein the sum of k, m, n, o, and p is greater than or equal to four; and the sum of k, m, and q is greater than zero, and A is a counterion, wherein the polyoxometalate is incorporated in the fabric, with the proviso that when A is a proton, the polyoxometalate is not the reaction product between $[V_kMo_mW_nNb_oTa_pM_qX_rO_s]^{y-}[A]$ and a pararosaniline compound, with the further proviso that the polyoxometalate is not silicomolybdenic acid or its sodium salt, phosphomolybdenic acid, ammonium chromododecanemolybdenate, ammonium salt of hydrogen hexamolybdocobaltic acid, para-tungstic acid or its ammonium salt or sodium salt, meta-tungstic acid or its ammonium salt or sodium salt, phosphotungstic acid or its salt, silicotungstic acid or its salt, dodecane tungstodicobaltic acid or its salt, phosphotungstomolybdenic acid or its salt, or phosphovanadomolybdenic acid or its salt, with the further proviso that when the fabric is carbon cloth, the polyoxometalate is not $H_5PV_2Mo_{10}O_{40}$.

In one embodiment, k is greater than or equal to one.

A pararosaniline compound is a compound having the structure IV

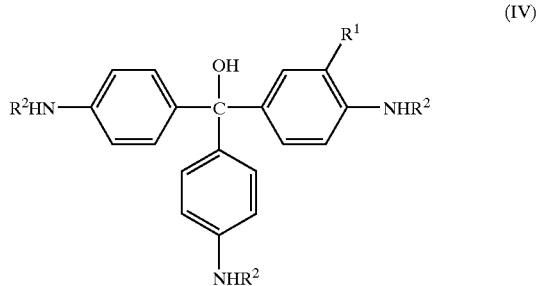

wherein $R^1$ is hydrogen or methyl and each $R^2$ is, independently, hydrogen or substituted or unsubstituted aryl. Examples of pararosaniline compounds not used in the present invention are disclosed in U.S. Pat. No. 4,444,592 to Ludwig, which is herein incorporated by reference in its entirety.

The invention further relates to an article comprising a polyoxometalate-modified fabric.

The invention further relates to a method of making a polyoxometalate-modified fabric, comprising contacting a fabric with a polyoxometalate to produce the polyoxometalate-modified fabric.

The polyoxometalate can be incorporated into the fabric or cellulosic fiber using techniques known in the art. Examples of techniques that can be used for incorporating the POM into a fabric or cellulosic fiber include, but are not limited to, depositing the POM on the surface of an existing fabric or cellulosic fiber, covalently bonding the POM to the fibers of the fabric or cellulosic fiber, impregnating or intimately mixing the POM with the fabric or cellulosic fiber, electrostatically bonding the POM to the fabric or cellulosic fiber, or datively bonding the POM to the fabric or cellulosic fiber via the coordination of a d- or f- block metal ion on the surface of the POM with a functional group on the fabric. In the case of electrostatically bonding the POM to the fabric or cellulosic fiber, the positively charged functional groups on the fabric or cellulosic fiber and the negatively charged POM can form an electrostatic bond. In one embodiment, when the counterion of the polyoxometalate is a proton, the fabric or cellulosic fiber can be protonated by the polyoxometalate to produce a positively charged fiber, which then electrostatically bonds to the polyoxometalate anion. In one embodiment, a cationic polymer can be used as a binding agent to incorporate an anionic polyoxometalate into an anionic fiber.

The polyoxometalates of the present invention can be incorporated in the fabric and the cellulosic fiber using a variety of techniques known in the art. In one embodiment, the fabric or cellulosic fiber is contacted with a mixture comprising the polyoxometalate and a solvent. The polyoxometalate can be soluble, partially soluble, or insoluble in the solvent, depending upon the polyoxometalate and solvent selected. In one embodiment, the solvent is water. In another embodiment, the solvent can be an organic solvent. Examples of organic solvents useful in the present invention include, but are not limited to, acetonitrile, acetone, toluene, carbon dioxide, xylenes, 1-methyl-2-pyrrolidinone, dimethyl sulfoxide, or an alcohol, such as methanol, ethanol, 1-propanol, or 2-propanol. In another embodiment, the solvent can be used in supercritical drying technology known in the art, which results in a finely-divided, high surface-area deposited polyoxometalate on the fabric or cellulosic fiber.

In one embodiment, the mixture is from 0.1 to 20% by weight polyoxometalate and from 80 to 99.9% by weight water, preferably from 0.3 to 15% by weight polyoxometalate and 85 to 99.7% water. Generally, the fabric or cellulosic fiber is dipped or immersed into the mixture containing the POM for several hours to days at a temperature of from 0° C. to 100° C., preferably for 2 hours to 2 days at from 25° C. to 80° C. In another embodiment, the POM can be admixed with a resin or adhesive, and the resultant adhesive is applied to the surface of or admixed with the fabric or cellulosic fiber.

Typically, once the fabric or cellulosic fiber has been contacted with the POM, the polyoxometalate-modified fabric or cellulosic fiber is dried in order to remove residual solvent. In one embodiment, the polyoxometalate-modified fabric or cellulosic fiber is heated from 0° C. to 220° C. at or below atmospheric pressure, preferably from 25° C. to 100° C. In another embodiment, the polyoxometalate-modified fabric or cellulosic fiber is dried in vacuo (i.e., less than or equal to 10 torr). In yet another embodiment, the polyoxometalate-modified fabric or cellulosic fiber is dried under supercritical conditions.

EXAMPLES

The following examples are put forth so as to provide those of ordinary skill in the art with a complete disclosure and description of how the methods and products claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, target odorants/toxics are expressed in parts per million, temperature is in ° C. or is at ambient temperature and pressure is at or near atmospheric.

The term "consumption" refers to the removal or adsorption of a contaminant or contaminants from the gas phase or the conversion of the contaminant or contaminants to another compound(s) that is less toxic or nontoxic and/or is less malodorous or not malodorous.

General Considerations

Materials. The polyoxometalate $H_5PV_2Mo_{10}O_{40}$ (1), $H_4PVMo_{11}O_{40}$ (2), and $H_6PV_3Mo_9O_{40}$ (3) were synthesized and purified following the procedure disclosed in Pettersson et al., *Inorg. Chem.* 1994, 33, pp. 982, and Tsigdinos et al., *Inorg. Chem.*, 1968, 7, pp. 437–441. $^{51}V$ and $_{31}P$ NMR were used to check the purity. The samples of Smoklin® (the brand name of a cloth manufactured by Asahi Chemical Industry Company, Japan, made mainly from polyacrylic yarn), acid-dyeable polyacrylic fiber and the "deep-dye" nylon fiber with $NH_2$ groups on the polymer ends were tested. The samples of cotton cloth were cut from a common 100% cotton T shirt after laundering. The samples of paper were obtained from Fisher Scientific. All samples were submitted to vacuum and then heated, or washed and then submitted to vacuum and then heated before use. All solvents used were purchased from Fisher or Burdick & Jackson company and had purities of greater than 99%. Acetaldehyde was obtained from Aldrich and exhibited purities greater than 99.9%. Argon, helium, and oxygen were ordered from Specialty Gases (greater than 99.5%). The gases ethane (Matheson), methyl mercaptan (Matheson) and ammonia (Air Products) were all of greater than 99% purity. All chemicals purchased were used as received, except acetaldehyde which was protected under Ar in the freezer to minimize adventitious autoxidation (radical chain oxidation by $O_2$) or other possible reactions.

Instrumentation. All reactions involving $CH_3CHO$ and $CH_3SH$ were monitored using a Hewlett-Packard 5890 gas chromatograph equipped with flame ionization detectors and a HP-PLOT Q divinyl benzene/styrene porous polymer capillary column. The consumption of $NH_3$ was detected by Sensidyne®/Gastec detector tube systems. $^{51}V$ NMR measurements were carried out on a 500-MHZ General Electric GN500 Spectrometer. $^{31}P$ NMR measurements were carried out on a 400-MHZ Varian Inova 400 Spectrometer. The diffuse reflectance infrared fourier transform spectroscopy (DRIFT) measurements for powdered $H_5PV_2Mo_{10}O_{40}$ and fabric systems were conducted using a Nicolet 510 FT-IR spectrometer. The scanning electron microscopy (SEM) experiments were carried out on a ISI DS-130/LaB$_6$EM. Elemental analysis were provided by E+R Microanalytical Laboratory, Inc.

Preparation of Fabrics with Supported $H_5PV_2Mo_{10}O_{40}$ (1). 1-Smoklin® cloth and 1-cotton cloth were prepared as follows: a 2-g sample of cloth was immersed in various aqueous solutions of 1 at room temperature. After 24 h impregnation, the cloth was dried at room temperature first in the air for 2 days and then in vacuo for another 2 days. Preparation for 1-acrylic and 1-nylon fibers: the nylon and acrylic fibers were washed in boiling 2-propanol for 4 h and then dried in vacuo at 323 K before use. Representative 2 g samples were then immersed in various aqueous solutions of 1 at 353 K for 2 h and then at room temperature for 1 day. Most of the water or excess solution was removed using a rotary evaporator or by filtration at room temperature. The 1-nylon or 1-acrylic samples were then dried at room temperature first in the air overnight and then in vacuo for 2 days. The percentages of 1 on the cloth or fibers were determined by both weight difference and elemental analysis (by E+R Microanalytical Laboratory, Inc.).

Preparation of POM-Filter Paper. A 0.6-g sample of paper was immersed in various aqueous solutions of 1, 2, and 3 at room temperature for a few hours until the POM-paper sample appeared dry by visual inspection. The resulting POM-paper sample was then dried in vacuo at room temperature overnight. In a control experiment, the unmodified paper was also treated with water and dried under identical conditions.

Comparison of Fabrics Unmodified or Modified with 1 in the Aerobic Oxidation of $CH_3CHO$ and $CH_3SH$. In all reactions, 0.5 g of 1-modified or unmodified cloth or fiber was hung in a 250-mL round-bottom flask covered with aluminum foil and sealed with a septum stopper. This apparatus was taken through three degas/gas cycles with Ar, evacuated and then purged with $O_2$. Next, 25 μl of gaseous $CH_3CHO$ (or 50 μl $CH_3SH$) and 25 μl $C_2H_6$ (internal standard) were added to the flask to start the reaction. The reactions were stirred using a digital stirrer at 1200 rpm and maintained at room temperature under 1 atm of $O_2$. For the oxidation of $CH_3SH$, reactions were carried out in three steps. After 20 h of the above reaction or no detectable $CH_3SH$ remaining in gas phase (the first step), an additional 500 μl $CH_3SH$ was then added to the apparatus to continue the reaction in the second step. An additional 500 μl $CH_3SH$ was added to the apparatus to initiate the reaction in the third step after 20 hr reaction of the second step. In all reactions, gaseous aliquots (1-mL) were extracted at various times and analyzed by GC. Blank control reactions with the materials (modified or unmodified) absent from the otherwise identical reaction systems were run at the same time. All reactions were run in duplicate to assess reproducibility and the averages reported.

Comparison of Paper Unmodified and Modified with 1 in the Aerobic Oxidation of $CH_3SH$ and $CH_3CHO$. In all reactions, 0.1 g of 1-paper or unmodified filter paper was hung in a 250-mL round-bottom flask covered with aluminum foil and sealed with a septum stopper. This apparatus was taken through three degas/gas cycles with Ar, evacuated and then purged with $O_2$. Next, 0.75 mL of gaseous $C_2H_6$ (internal standard) and 1.5 mL of gaseous $CH_3SH$ were added to the flask to initiate the $CH_3SH$ reaction. Alternatively, 0.025 mL of gaseous $C_2H_6$ (internal standard) and 0.025 mL of gaseous $CH_3CHO$ were injected into the flask to initiate the $CH_3CHO$ reaction. The reactions were stirred at 1,200 rpm using a digital stirrer and maintained at ambient temperature under 1 atm of $O_2$ for 3 hrs. During the reaction, gaseous 1-mL aliquots were removed at various times and analyzed by GC to determine the concentration of remaining $CH_3SH$ or $CH_3CHO$ in the gas phase. All reactions were run in duplicate to assess reproducibility and the averages reported.

Evaluation of Reusability of 1-Modified Fabrics in the Aerobic Oxidation of $CH_3CHO$. The reactions were run as described above. The 1-fabrics were recovered by treating the fabrics in vacuo at room temperature for 2 days. The reactions involving these materials were then run again under the conditions identical to those in the first run.

Comparison of Fabrics Unmodified or Modified with 1 in the Removal of $NH_3$. In all reactions, 0.5 g of 1-modified or unmodified cloth or fiber was hung in a 5-L round-bottom flask sealed with a septum stopper. This apparatus was taken through three degas/gas cycles with Ar. Next, 1-mL of gaseous $NH_3$ was injected into the flask to start the reaction. The reactions were stirred using a digital stirrer at 500 rpm and maintained at room temperature under 1 atm of Ar. After 1 hr reaction, 100-mL gaseous aliquots were extracted by the detector tube to analyze the concentration of the remaining $NH_3$. All reactions were run in duplicate.

Evaluation of Fabrics Unmodified or Modified with 1 in the Deodorization of a Simulated Polluted Atmosphere ($CH_3CHO$, $CH_3SH$, and $NH_3$). The reaction apparatus was prepared following almost the same procedure as described above, except that 500-mL flask was used. $C_2H_6$ (50 μl), $CH_3CHO$ (50 μl), $CH_3SH$ (500 μl) and $NH_3$ (500 μl) were injected simultaneously into the apparatus to start the reaction. The reactions were stirred using a digital stirrer at 1,200 rpm and maintained at room temperature under 1 atm of $O_2$. All reactions were run in duplicate to assess reproducibility and the averages reported.

Evaluation of Paper and POM-Paper with a Simulated Polluted Atmosphere. The reaction apparatus was prepared following the same procedure described above, except that a 500-mL flask was used. The gases $C_2H_6$ (1 mL), $CH_3CHO$ (0.5 mL), $CH_3SH$ (2 mL) and $NH_3$ (0.5 mL) were injected simultaneously into the apparatus to start the reaction. The flask contents were stirred using a digital stirrer at 1,200 rpm and maintained at room temperature under 1 atm of $O_2$. After the reaction, gaseous 1-mL aliquots were removed and analyzed by GC to determine the concentration of remaining $CH_3CHO$ and $CH_3SH$ in the gas phase. The concentration of remaining $NH_3$ was checked by Sensidyne®/Gastec detector tube.

Figure 2A:
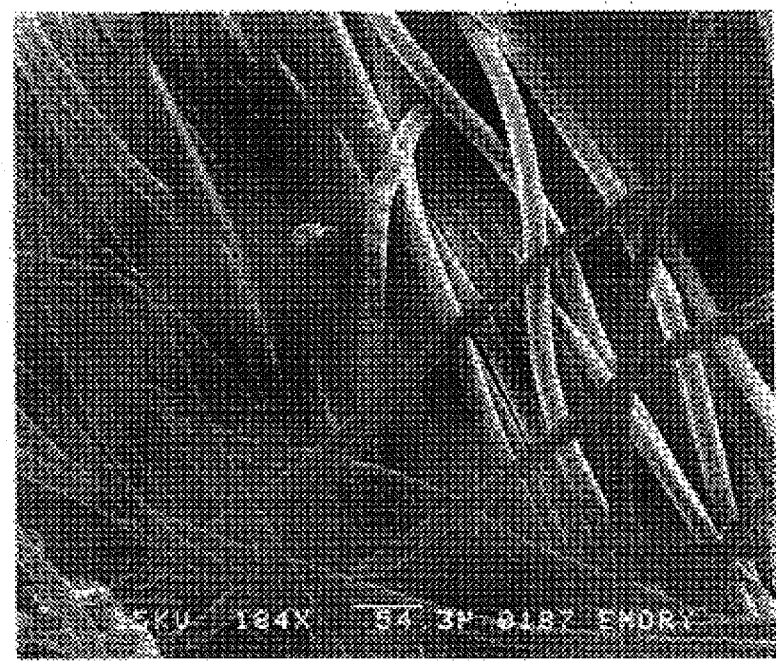
FIG. 2 shows the SEM pictures of acrylic (top) and 1-acrylic (5 wt % of 1, bottom).
Figure 2B:

Characterization. The DRIFT spectra of $H_5PV_2Mo_{10}O_{40}$ (1) modified Smoklin®, cotton cloth, acrylic fiber and nylon fiber are all similar to that of the unsupported $H_5PV_2Mo_{10}O_{40}$ powder in the typical IR range (600–1200 $cm^{-1}$) for polyoxometalates, indicating that 1 is present on the surface of all the modified fabrics (see FIG. 1, 5 wt % 1-acrylic fiber). The SEM pictures in FIG. 2 demonstrate that clusters of 1 are formed unevenly on the surface of the fabrics during the preparation of 1-acrylic. The size of most clusters of 1 on 1-Smoklin® (5 wt %) and 1-acrylic (5 wt %) are in the 1–5 μm range.

Gas Phase Reactions. In all gas phase reactions, the overall observed consumption of the reagents reflects both the reactions of the reagents and their adsorption on the glass and cloth surfaces.

Example 1

Figure 3:
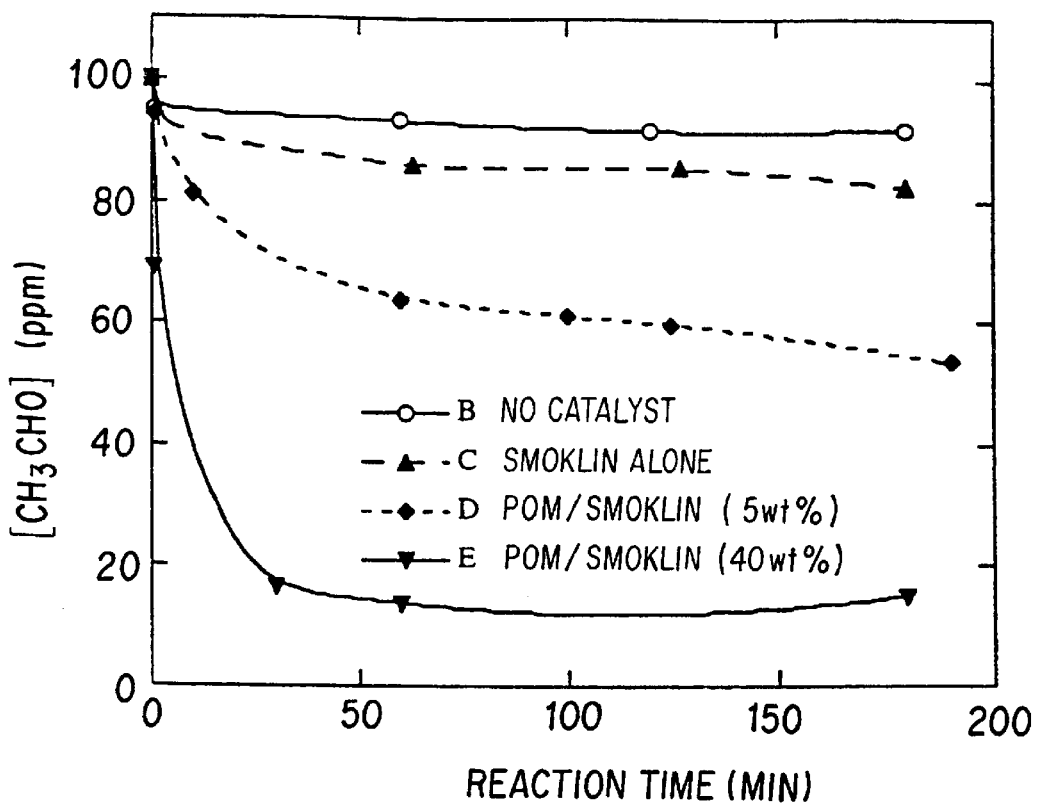
FIG. 3 shows the aerobic oxidation of gaseous $CH_3CHO$ by Smoklin® and Smoklin® with adsorbed 1.

Comparison of Catalytic Efficiencies of the 1-Fabrics in the Aerobic of Oxidation $CH_3CHO$. All gas phase reactions were run at room temperature and under 1 atm $O_2$ pressure. FIG. 3 displays the consumption (concentration versus time) curves when no catalyst, Smoklin® alone and 1-Smoklin® (with both 5 wt % and 40 wt % of 1) were used under otherwise identical reaction conditions. A comparison of the curves for the Smoklin® alone and the catalyst-free control experiment indicates that the Smoklin® has no significant activity. For the Smoklin® modified by 1, significant activity is observed even when the weight percentage of 1 is as low as 5 wt %. Additionally, FIG. 3 reveals that 1-Smoklin® removes a contaminant from the gas phase at a much higher rate than unmodified Smoklin®, which is another advantage of the present invention.

Table 1 summarizes the results for different cloth and fiber systems in 3 hr reactions. All the unmodified fabrics, the 1-nylon (even when the present of 1 is as high as 15 wt %) and the 1-cotton cloth (5 wt % of 1) exhibit little or no activity. In contrast, significant activity is demonstrated for the 1-Smoklin® (5 wt % of 1), the 1-acrylic fiber (5 wt % of 1) and the 1-cotton cloth (15 wt % of 1) with no detectable $CH_3COOH$ present in gas phase.

TABLE 1

Removal of $CH_3CHO$ from the Gas Phase by Polyoxometalate-Modified Fabrics.[a]

| Fabric | Consumption of $CH_3CHO$ (%)[b] |
|---|---|
| None[c] | 9 |
| Smoklin ® | 15 |
| 1-Smoklin ® (5 wt % 1) | 49 |
| 1-Smoklin ® (10 wt % 1) | 55 |
| 1-Smoklin ® (40 wt % 1) | 89 |
| acrylic | 13 |
| 1-acrylic (5 wt % 1) | 62 |
| cotton | 26 |
| 1-cotton (5 wt % 1) | 30 |
| 1-cotton (15 wt % 1) | 56 |
| nylon | 19 |
| 1-nylon (15 wt % 1) | 22 |

[a]Reaction conditions: $CH_3CHO$ (100 ppm) and $C_2H_6$ (internal standard, 100 ppm) were stirred at 1200 rpm in a 250-mL flask under 1 atm of $O_2$ at room temperature for 3 hrs. The fabric (0.5 g, modified or unmodified with 1 ($H_5PV_2Mo_{10}O_{40}$)) was hung in the flask covered with aluminum foil and sealed with a septum stopper. All the values in Table 1 are averages of two experiments.
[b]Refers to the overall $CH_3CHO$ consumption in the gas phase.
[c]Refers to the consumption of $CH_3CHO$ by the reaction vessel.

Example 2

Evaluation of Reusability of the 1-Fabrics in the Aerobic Oxidation of $CH_3CHO$. Table 2 illustrates that the reusability of 1-Smoklin® (5 wt % and 40 wt %) and 1-acrylic (5 wt %) as catalysts in the aerobic oxidation of $CH_3CHO$ is very high. The catalytic activity of 1-Smoklin® does not decrease significantly upon the recovery treatment in vacuo and reuse.

TABLE 2

Reusability of $H_5PV_2Mo_{10}O_{40}$ (1)-Modified Fabrics in the Removal of $CH_3CHO$ in the Gas Phase.[a]

| | Consumption % of $CH_3CHO$[b] | | |
|---|---|---|---|
| Fabric | first use | second use[c] | third use[d] |
| 1-Smoklin ® (5 wt %) | 49 | 40 | 42 |
| 1-Smoklin ® (40 wt %) | 89 | 82 | 83 |
| 1-acrylic (5 wt %) | 62 | 30 | 32 |

[a]Reaction conditions as described in Table 1.
[b]Refers to the overall $CH_3CHO$ consumption in the gas phase. All values in Table 2 are an average of two experiments.
[c]After the first reaction, the used fabrics were placed in vacuo at room temperature for 2 days to remove all adsorbed compounds. The recovered fabrics were then used for a new reaction under the same conditions as in the first run.
[d]The same procedures described in "c" were used.

Example 3

Comparison of Catalytic Activities of the 1-Fabrics in the Aerobic Oxidation of $CH_3SH$. Table 3 summarizes the catalytic activities of different polyoxometalate-modified fabrics of the present invention in the oxidation of $CH_3SH$. All of the unmodified fabrics and 1-cotton cloth (5 wt %) exhibit little or no activity, while 1-Smoklin® (5 wt %), 1-acrylic (5 wt %) and 1-cotton cloth (15 wt %) all possess significant activities. Not wishing to be bound by theory, the high activities observed for the anaerobic reactions involving 1-Smoklin® (5 wt %) and 1-acrylic (5 wt %) indicate that 1 most likely functions as a redox catalyst, not simply as a radical chain initiator in the aerobic reactions. The reversible redox chemistry of 1 accounts for the better activity observed in the presence of $O_2$. In all the reactions containing 1, dimethyl disulfide ($CH_3SSCH_3$) is present as the predominant product in gas phase, while in the blank and control reactions, no detectable product exists.

TABLE 3

Removal of $CH_3SH$ in the Gas Phase by 1-Modified Fabrics.[a]

| | Consumption % of $CH_3SH$[b] | | |
|---|---|---|---|
| Fabric | Step 1 200 ppm[c] at 3 hr | Step 2 2000 ppm[d] at 2 hr | Step 3 2000 ppm[e] at 2 hr |
| Blank ($O_2$)[f] | 36 | 11 | — |
| Smoklin ® ($O_2$) | 30 | 12 | — |
| 1-Smoklin ® (5 wt %, Ar) | 100 | 85 | 14 |
| 1-Smoklin ® (5 wt %, $O_2$) | 100 | 96 | 47 |
| acrylic ($O_2$) | 27 | 9 | — |
| 1-acrylic (5 wt %, Ar) | 100 | 79 | 11 |
| 1-acrylic (5 wt %, $O_2$) | 100 | 100 | 100 |
| Cotton ($O_2$) | 33 | 11 | — |
| 1-Cotton (5 wt %, $O_2$) | 44 | — | — |
| 1-Cotton (15 wt %, $O_2$) | 100 | 52 | 13 (3 hr) |

[a]Reaction conditions: $CH_3SH$ and $C_2H_6$ (internal standard, 100 ppm) were stirred at 1200 rpm in a 250-mL flask under 1 atm of $O_2$ or Ar at room temperature. The fabric (0.5 g, modified or unmodified with 1) was hung in the flask covered with aluminum foil and sealed with a septum stopper. All values in Table 3 are averages of two experiments.
[b]Based on the overall $CH_3SH$ comsumption in the gas phase.
[c]Step 1: 200 ppm of $CH_3SH$ was added.
[d]Step 2: an additional 2000 ppm of $CH_3SH$ was added after step 1.
[e]Step 3: an additional 2000 ppm of $CH_3SH$ was added after step 2.
[f]Indicates uptake of $CH_3SH$ by the reaction vessel.

Example 4

Comparison of $NH_3$ Removal Capabilities of the 1-Fabrics. The results in Table 4 demonstrate that 1 modified Smoklin®, acrylic fiber and cotton cloth are much more active in deodorizing $NH_3$ than the untreated fabrics. The mole ratios of 1 to $NH_3$ are 1:3.1 and 1:1 for the reactions of the fabrics modified with 5 wt % and 15 wt % of 1, respectively. Not wishing to be bound by theory, the mechanism likely involves the acid-base process in equation 1.

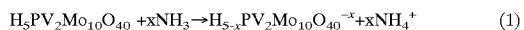

$$H_5PV_2Mo_{10}O_{40} + xNH_3 \rightarrow H_{5-x}PV_2Mo_{10}O_{40}^{-x} + xNH_4^+ \quad (1)$$

TABLE 4

Removal of $NH_3$ in the Gas Phase by 1-Modified Fabrics.[a]

| Fabric | Consumption % of $NH_3$[b] |
|---|---|
| Smoklin ® | 23 |
| 1-Smoklin ® (5 wt %) | 98 |
| acrylic | 30 |
| 1-acrylic (5 wt %) | 97 |
| cotton | 36 |
| 1-cotton (5 wt %) | 69 |
| 1-cotton (15 wt %) | 99 |

[a]Reaction conditions: 200 ppm $NH_3$ was stirred at 500 rpm in a 5-L flask under 1 atm of Ar at room temperature for 1 hr. The fabric (0.5 g, modified or unmodified with 1) was hung in the flask sealed with a septum stopper. All values in Table 4 are averages of two experiments.
[b]Based on the overall $NH_3$ consumption in the gas phase.

Example 5

Comparison of Overall Deodorizing Capabilities of the 1-Fabrics. The deodorizing efficiencies of 1-modified fabrics were further evaluated in the contaminated atmosphere simulated by the simultaneous presence of $CH_3CHO$, $CH_3SH$ and $NH_3$. The results in Table 5 indicate that 1-modified Smoklin®, acrylic and cotton cloth are much more effective than the corresponding unmodified fabrics.

TABLE 5

Simultaneous Removal of $CH_3CHO$, $CH_3SH$ and $NH_3$ in the Gas Phase by 1- Modified Fabrics.[a]

| | Consumption %[b] | | |
|---|---|---|---|
| Fabric | $CH_3CHO$ | $CH_3SH$ | $NH_3$ |
| Smoklin ® | 31 | 9 | 51 |
| 1-Smoklin ® (5 wt %) | 84 | 68 | 100 |
| acrylic | 27 | 6 | 47 |
| 1-acrylic (5 wt %) | 63 | 92 | 100 |
| cotton | 33 | 10 | 78 |
| 1-cotton (15 wt %) | 86 | 66 | 100 |

[a]Reaction conditions: $CH_3CHO$ (100 ppm), $CH_3SH$ (500 ppm), $NH_3$ (500 ppm) and $C_2H_6$ (internal standard, 100 ppm) were stirred at 1200 rpm in a 500-mL flask under 1 atm of $O_2$ at room temperature for 3 hrs. The fabric (0.5 g, modified or unmodified with 1) was hung in the flask covered with aluminum foil and sealed with a septum stopper. All values in Table 5 are averages of two experiments.
[b]Refers to the overall consumption of the reagents in the gas phase.

The collective data from the gas phase reactions indicate that modifying the cloth or fiber systems with 1 can improve their activity for removing both oxidizable organic compounds by reaction with $O_2$, and basic compounds by proton donation from the polyoxometalate.

Example 6

Comparison of Catalytic Efficiencies in the Aerobic of Oxidation $CH_3SH$ by 1-Paper. Prior to all reactions, both the unmodified paper and the 1-paper were prepared using identical protocols, except that for the unmodified paper, only 1-free water was present in the immersion step. In Table 6, the catalytic activity of 1-paper is compared with the unmodified filter paper for the removal of $CH_3SH$. The results indicate that the deposition of 1 on to the paper definitely increases the paper's reactivity. The amount of 1 incorporated into the paper is an important parameter for the reactivity. As for the 1-fabrics, dimethyl disulfide was the main detectable product in the 1-paper reactions, implying that the same mechanism was involved. A color change also accompanied this redox reaction (the 1-paper turned from light orange to dark green). The control reaction using the unmodified paper reaction produced no detectable dimethyl disulfide or other products.

TABLE 6

The Aerobic Oxidation of CH$_3$SH in gas phase catalyzed by 1-Paper.[a]

| Sample | % Consumption of CH$_3$SH[b] | Turnovers[c] |
|---|---|---|
| Paper | 10 | — |
| 30 wt % 1-Paper | 16 | 0.6 |
| 37 wt % 1-Paper | 45 | 1.4 |
| 45 wt % 1-paper | 61 | 1.6 |

[a]Reaction conditions: CH$_3$SH (6000 ppm) and C$_2$H$_6$ (internal standard, 3000 ppm) were stirred at 1200 rpm in a 250-mL flask under 1 atm of O$_2$ at room temperature for 3 hrs. Filter paper (0.1 g, unmodified or modified with 1) was hung in the flask covered with aluminum foil and sealed with a septum stopper. All values are averages of two experiments.
[b]Based on the gas phase reactant.
[c]Turnovers = moles of CH$_3$SH consumed/moles of 1 incorporated into the paper.

Example 7

Removal in the Gas Phase of CH$_3$CHO by 1-Paper. Table 7 summarizes different efficiency of the unmodified and 1-modified paper in the removal of CH$_3$CHO in gas phase. Better removing efficiency was observed for the 1-paper than the untreated paper. As for the CH$_3$SH oxidation reaction, the amount of 1 deposited on the paper again influences the paper's reactivity.

TABLE 7

The Removal of CH$_3$CHO in gas phase by 1-Paper.[a]

| Sample | % Consumption of CH$_3$CHO[b] |
|---|---|
| Paper | 9 |
| 15 wt % 1-Paper | 12 |
| 30 wt % 1-Paper | 23 |
| 45 wt % 1-paper | 45 |
| 60 wt % 1-paper | 63 |

[a]Reaction conditions: CH$_3$CHO (100 ppm) and C$_2$H$_6$ (internal standard, 100 ppm) were stirred at 1200 rpm in a 250-mL flask under 1 atm of O$_2$ at room temperature for 3 hrs. Filter paper (0.1 g, unmodified or modified with 1) was hung in the flask covered with aluminum foil and sealed with a septum stopper. All values are averages of two experiments.
[b]Based on the gas phase reactant.

Example 8

Comparison of Overall Deodorizing Capabilities of POM-Paper. Table 8 illustrates the reactive behavior of the POM-paper and POM-free paper in the polluted air model (CH$_3$CHO, CH$_3$SH and NH$_3$ all present in the atmosphere). The results indicate that 1-paper, 2-paper, and 3-paper are much more effective than the corresponding POM-free paper in removing all the target gaseous molecules. More importantly, the data indicate that the paper modified with different POM have different selectivity, implying that the rates of different pollutant uptake processes vary with the POM-paper.

TABLE 8

Simultaneous Removal of CH$_3$CHO, CH$_3$SH and NH$_3$ in the Gas Phase Catalyzed by POM-paper.[a]

| | % Consumption, Turnover[b] | | |
|---|---|---|---|
| | CH$_3$CHO | CH$_3$SH | NH$_3$ |
| paper | 28, — | 9, — | 65, — |
| 1-paper (60 wt %) | 87, 0.57 | 93, 2.4 | 100, — |
| 2-paper (60 wt %) | 94, 0.62 | 87, 2.3 | 100, — |
| 3-paper (60 wt %) | 77, 0.51 | 96, 2.5 | 100, — |

[a]Reaction conditions: CH$_3$CHO (1,000 ppm), CH$_3$SH (4,000 ppm), NH$_3$ (1,000 ppm) and C$_2$H$_6$ (internal standard, 2,000 ppm) were stirred at 1,200 rpm in a 500-ml flask under 1 atm of O$_2$ at ambient temperature for 2 hours. Paper (0.1 g, unmodified or modified with 1 (H$_5$PV$_2$Mo$_{10}$O$_{40}$), 2 (H$_4$PVMo$_{11}$O$_{40}$), or 3 (H$_6$PV$_3$Mo$_9$O$_{40}$)) was hung in the flask covered with aluminum foil and sealed with a septum stopper. All values are averages of two experiments.
[b]% Consumption is based on the overall consumption of the reagents in gas phase; Turnovers = moles of substrate consumed/moles of POM incorporated into the paper.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only.

What is claimed:

1. A polyoxometalate-modified fabric, comprising a fabric and a polyoxometalate incorporated into the fabric, said polyoxometalate having the formula [Y V$_x$Z$_{12-x}$O$_{40}$] [A], wherein Y is phosphorus, silicon, or aluminum; Z is tungsten or molybdenum; x is from 1 to 6, and A is a counterion, with the proviso that when the fabric is carbon cloth, the polyoxometalate is not H$_5$PV$_2$Mo$_{10}$O$_{40}$.

2. An article comprising the polyoxometalate-modified fabric of claim 1.

3. The article of claim 2, wherein the article is garment, drapery, carpet, or upholstery.

4. The fabric of claim 1, wherein A comprises a quaternary ammonium cation; proton; alkali metal cation; alkaline earth metal cation; ammonium cation; d- or f-block metal complex; or a combination thereof.

5. The fabric of claim 1, wherein the polyoxometalate comprises H$_5$PV$_2$Mo$_{10}$O$_{40}$ when the fabric is not carbon cloth.

6. The fabric of claim 1, wherein the fabric is prepared from a fiber comprising polyamide, cotton, polyacrylic, polyacrylonitrile, polyester, polyvinylidine, polyolefin, polyurethane, polytetrafluoroethylene, or carbon cloth, or a combination thereof.

* * * * *